(12) United States Patent
Tanaka et al.

(10) Patent No.: US 7,634,062 B2
(45) Date of Patent: Dec. 15, 2009

(54) CIRCULAR ACCELERATION APPARATUS, ELECTROMAGNETIC WAVE GENERATOR AND ELECTROMAGNETIC-WAVE IMAGING SYSTEM

(75) Inventors: Hirofumi Tanaka, Tokyo (JP); Takahisa Nagayama, Tokyo (JP); Nobuyuki Zumoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 118 days.

(21) Appl. No.: 11/860,965

(22) Filed: Sep. 25, 2007

(65) Prior Publication Data

US 2008/0079372 A1   Apr. 3, 2008

(30) Foreign Application Priority Data

Sep. 26, 2006   (JP) .............................. 2006-260419

(51) Int. Cl.
*H01J 23/00* (2006.01)
(52) U.S. Cl. ....................................... 378/137; 315/500
(58) Field of Classification Search ................ 378/124, 378/137, 119; 315/500, 501, 502, 503, 507
See application file for complete search history.

(56) References Cited

U.S. PATENT DOCUMENTS 5,471,516 A * 11/1995 Nunan .......................... 378/65
5,680,018 A    10/1997 Yamada
2006/0056596 A1 *  3/2006 Mori et al. .................. 378/138

FOREIGN PATENT DOCUMENTS

| JP | 8-195300 | 7/1996 |
|----|----------|--------|
| JP | 2004-296164 | 10/2004 |

OTHER PUBLICATIONS

Tohru Kamei, et al., "Accelerator Science", Published by Maruzen Co., Ltd., 1993, pp. 39-43.

* cited by examiner

*Primary Examiner*—Hoon Song
(74) *Attorney, Agent, or Firm*—Oblon, Spivak, McClelland, Maier & Neustadt, L.L.P.

(57) ABSTRACT

An objective is to provide a circular acceleration apparatus that can accelerate higher currents as well as avoid complex controlling of a deflecting magnetic field generated by an electron deflection unit. The circular acceleration apparatus is provided, which comprising a circular accelerator 2 including an electron acceleration unit 13 and a deflection-magnetic-field generating unit 14; an electron generator 1, to which a pulsed voltage is applied, to generate electrons for injecting to the circular accelerator 2; and a circuit element which generates the pulsed voltage for providing to the electron generator 1 by making the pulsed voltage applied to the electron generator 1 have at least one of a slow rising edge and a slow falling edge.

17 Claims, 9 Drawing Sheets

CIRCULAR ACCELERATION APPARATUS, ELECTROMAGNETIC WAVE GENERATOR AND ELECTROMAGNETIC-WAVE IMAGING SYSTEM

BACKGROUND OF THE INVENTION

1. Field of the Invention

The present invention relates to a circular acceleration apparatus that can accelerate large-current electron beams, an electromagnetic wave generator that generate electromagnetic waves such as X-rays by making electrons accelerated by the circular acceleration apparatus collide with a target, and an electromagnetic-wave imaging system that produce radioscopic images of human bodies, semiconductors and the like, using X-rays and such generated by the electromagnetic wave generators.

2. Description of the Related Art

In the description below, it is assumed that a circular acceleration apparatus is configured with a circular accelerator, an electron injection unit and a power supply necessary for operating them. The circular accelerator handles electrons generated by an electron generator as injection electrons, and accelerates the injection electrons until they have a predetermined energy, while making them move in their orbits; it may not necessarily be circular. For convenience, the term "circular" is given because electrons circulate in orbits.

In electromagnetic wave generators that use the circular accelerators to generate X-rays and such, betatron accelerators and synchrotron accelerators such as electron storage rings have been used as the circular accelerators. However, when the betatron accelerators are used, increase of current is difficult due to effects of Coulomb repulsion between electrons, resulting in a low electromagnetic wave strength of X-rays and such generated by making electrons collide with a target, so that it has been difficult to apply to industry and medical fields the electromagnetic wave generators using the accelerators. When the synchrotron accelerators are used as radiation sources, the electromagnetic waves generated thereby are intense, but have low energy; it has been difficult to apply those to the industry and medical fields. Also, when synchrotron accelerators are used in order to generate highly-energized electromagnetic waves, a method of not using synchrotron radiation, but making electrons collide with a target is to be adopted; however, the method brings the same difficulties as those when the betatron accelerators are used, in that it is difficult to increase current, so that the strength of the generated electromagnetic waves such as X-rays becomes low; therefore, it has been difficult to apply to the industry and medical fields the electromagnetic wave generators using the synchrotron accelerators as highly energized ones.

In order to improve the situation described above, an electromagnetic wave generator using a so-called hybrid accelerator has been proposed in Japanese Patent Laid-Open No. 2004-296164 (Patent Document 1). The hybrid accelerator is the one that employs such an acceleration method as follows: while an acceleration means is accelerating electrons from an instant when their injection into the accelerator begins, a deflecting magnetic field generated by deflection electromagnets included in the accelerator is kept constant during an injection period, and is controlled to change after finishing the injection. In this accelerator, stable electron orbits exist spreading out over a broad radial range; therefore, when electrons are injected in the way described above, the electrons move stably in orbits each having a different diameter depending on their injected instances during the injection period. Therefore, the accelerator makes the electrons move in orbits spreading over a wide orbital range. Thereby, the spatial density of electrons can be lowered, resulting in less Coulomb repulsion among the electrons, which will enable large-current acceleration.

Figure 10:
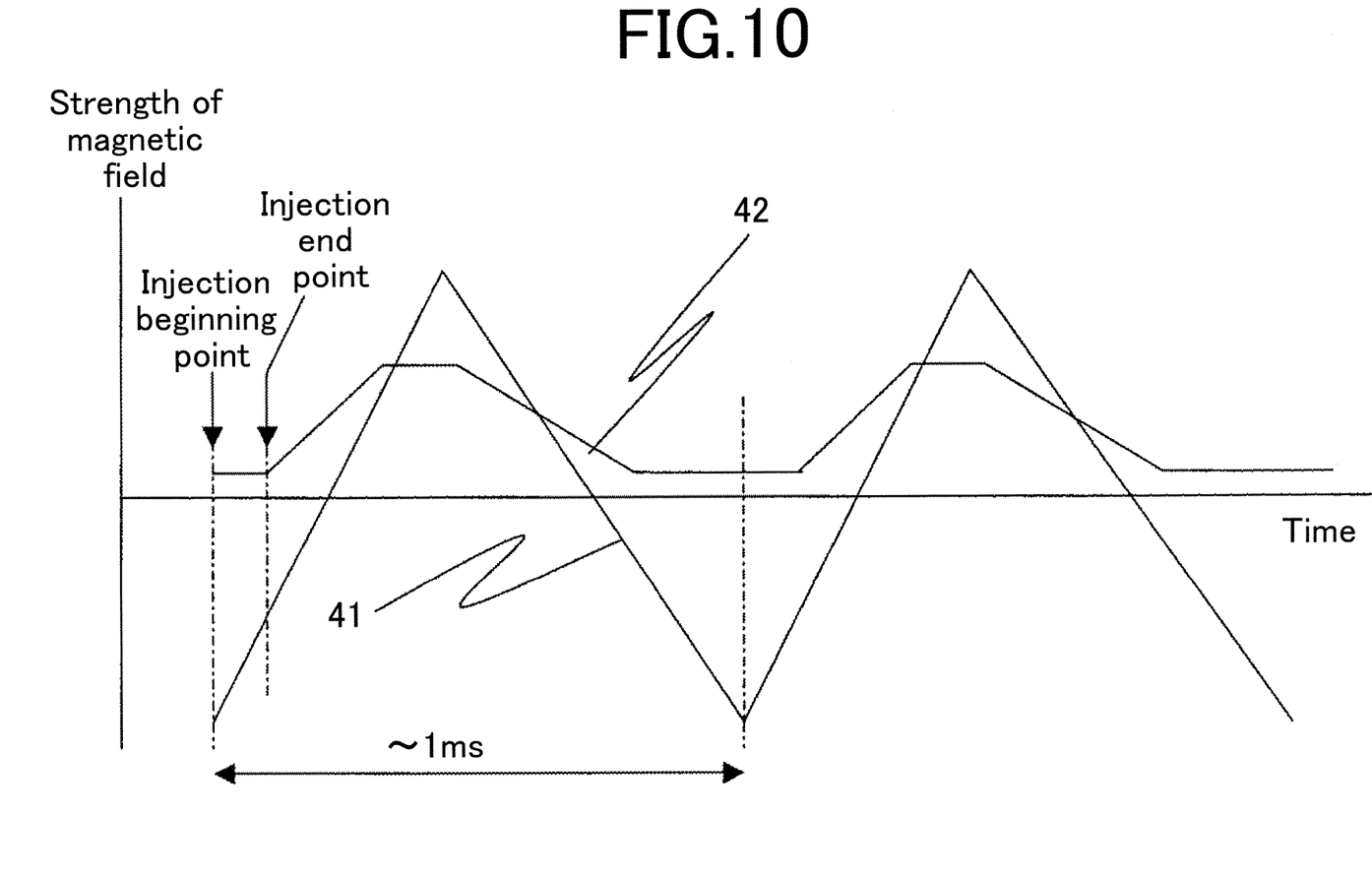
FIG. 10 is a diagram illustrating waveforms of strengths of electromagnetic fields generated by the electron acceleration unit and the electron deflection unit in a circular acceleration apparatus related to background arts.

The hybrid accelerator adopts as an accelerating means, so-called induction acceleration by an electric field that an accelerating magnetic field induces. FIG. 10 shows variations with time of deflection-magnetic-field strength and acceleration-magnetic-field strength according to the invention of Patent document 1. In FIG. 10, '41' is the acceleration-magnetic-field strength variation with respect to time, '42', that of the deflection-magnetic-field strength; it is assumed that injecting operations are performed in a pulsational manner. Here, "injecting operations are performed in a pulsational manner" means that each injection is performed during a predetermined period after a pulse of a rectangular waveform reaches its peak wave-height value. More specifically, because the pulse rises to its peak value immediately after it has been generated, the injection period is set as follows: injection starts after a specific time—from an instant at which the pulse has been applied to an instant at which the pulse reaches its peak—has passed, and continues until a specific time has elapsed while the pulse peak value is held. Because the acceleration-magnetic-field strength 41 begins to increase from an instant when the injection of electrons starts, the electrons have been accelerated from the instant when they have been injected. Meanwhile, the deflection-magnetic-field strength 42 is controlled to stay at a constant value from the instant of the injection start to an instant of the injection end; as soon as the injection ends, the strength 42 is controlled to begin to increase, similarly to the acceleration-magnetic-field strength 41. While the deflection-magnetic-field strength 42 stays at the constant value, the injected electrons that have the same energy as each other are accelerated immediately after their injection, and their deflection curvatures gradually become larger. Therefore, at the instant of injection end, each of the electrons has been accelerated differently depending on its injected instant during the injection period; the injection electrons move in orbits spreading out radially. Because the electrons continue to be thereafter accelerated so as to have a predetermined energy, the radially spread orbits are further expanded radially. After the end of the injection, the deflection-magnetic-field strength 42 increases; the degree of the orbit radial expansion usually becomes less than that during the injection. Once the electrons have been accelerated to have the predetermined energy, the radii of the electron orbits can be expanded by, for example, controlling the deflection-magnetic-field strength 42 at a constant value and the like.

When a target is placed in the way of an orbit having a predetermined radius out of the ones in which the electrons can move around stably, the radii of the electron orbits being changed, the electron beams can collide with the target in a controlled manner, so that electromagnetic waves such as X-rays are generated by the collision. Here, because the target has a certain area, the electrons moving in orbits within a specific radial range are ready to be capable of colliding with the target. Such orbits will be referred as collision orbits, hereinafter.

Even while the radii of the electron orbits are being changed, electrons are diverged radially and are moving in orbits; by gradually changing the radii of the orbits, the electron beams can continue to collide with the target, so that X-rays can be generated continuously. Here, all the electrons that have collided with the target do not always disappear, but electrons that have reduced energy remain there after their collision. Because in general, the residual electrons also have energies in the range of enabling stable movement in orbits, some of the electrons can be recharged with sufficient energy from the acceleration magnetic field every turn, so as to return to a collision orbit. Therefore, using the accelerator, electromagnetic waves can be generated efficiently utilizing electrons moving in orbits (refer to Patent document 1).

As has been described, in the accelerators, because the electrons have stable radially-spread-out orbits, causing less Coulomb repulsion between electrons, it becomes easy to accelerate large currents; because the position of the orbits can be changed, while maintaining conditions for electrons to move stably in orbits by controlling the acceleration-magnetic-field strength and the deflection-magnetic-field strength, it becomes possible for electrons moving in orbits to collide efficiently with the target. Thereby, it becomes possible to increase the strength of the electromagnetic wave such as X-rays generated by the accelerator. So far, a hybrid accelerator has been described as a typical example, it is not limited to the hybrid accelerator that current can be increased by increasing the radii of electron orbits. Any type of circular accelerator has more or less a certain radial range of orbits in which electrons move stably; therefore, it is also possible in a similar fashion to increase current by increasing the radii of the electron orbits. Meanwhile, some accelerators adopt an electric-field acceleration method instead of induction one using a magnetic field. In that case, the above description holds true if the term "acceleration-magnetic-field strength" is interchanged with the term "electric-field acceleration" in FIG. 10. However, during an electron injection period, a hybrid accelerator needs to control changes with time both the acceleration-magnetic-field strength and the deflection-magnetic-field strength so as to have predetermined relationships therebetween; it results in complex electromagnet-power-supply controlling in which the electron acceleration unit and the electron deflection unit generate magnetic fields, causing a problem in that the accelerator has been manufactured at high costs. The above problem has also existed when an electric field acceleration method as well as induction one is used as an electron acceleration means. In that case, it results in complexity of controlling power supply for the electric field acceleration and electromagnet-power-supply that lets the electron deflection unit generate magnetic fields, causing a problem in that the accelerator has been manufactured at high costs. Therefore, when it is intended to increase current in the circular accelerator according to the above-described method, it has been a common problem, not limited to the hybrid accelerator, that control of a power supply applying a high voltage to an electron acceleration unit and a power supply supplying currents to an electron deflection unit for generating a deflecting magnetic field becomes complex, causing high costs.

SUMMARY OF THE INVENTION

The present invention provides a circular acceleration apparatus comprising: a circular accelerator including an electron acceleration unit accelerating injected electrons, and a deflection-magnetic-field generating unit deflecting the orbits of the electrons accelerated by the electron acceleration unit; an electron generator, to which a pulsed voltage is applied, to generate electrons for injecting to the circular accelerator in respond to the pulsed voltage; and a circuit element which generates the pulsed voltage for providing to the electron generator by making the pulsed voltage applied to the electron generator have at least one of a slow rising edge and a slow falling edge.

Also the present invention provides a circular acceleration apparatus comprising: a circular accelerator including an electron acceleration unit accelerating injected electrons, and a deflection-magnetic-field generating unit deflecting the orbits of the electrons accelerated by the electron acceleration unit; and an electron generator, to which a pulsed voltage is applied, to generate electrons for injecting into said circular accelerator based on the voltage of the rising or falling edge of said pulsed voltage.

DETAIL DESCRIPTION OF THE PREFERRED EMBODIMENT

Hereinafter, embodiments according to the present invention are explained based on figures.

Embodiment 1

An embodiment according to the present invention is that orbit radii of electrons in a circular accelerator are enlarged by injecting into the circular accelerator electrons generated by an electron generator with their energies being varied. Applying this embodiment, even when the strength of a deflection magnetic field changes with respect to time in the same patterns as that of an acceleration magnetic field, it is possible to enlarge orbit radii of electrons that have been injected and accelerated, without controlling strength change with time of deflection magnetic field in a complicated manner as has been implemented in a conventional apparatus. Therefore, it becomes possible, in a simplified manner, to reduce substantially spatial density of orbiting electrons, enabling large-current acceleration and storage. Hereinafter, first an overall apparatus according to this embodiment will be outlined; then a method of varying energies of electrons generated by the electron generator will be described.

Figure 1:
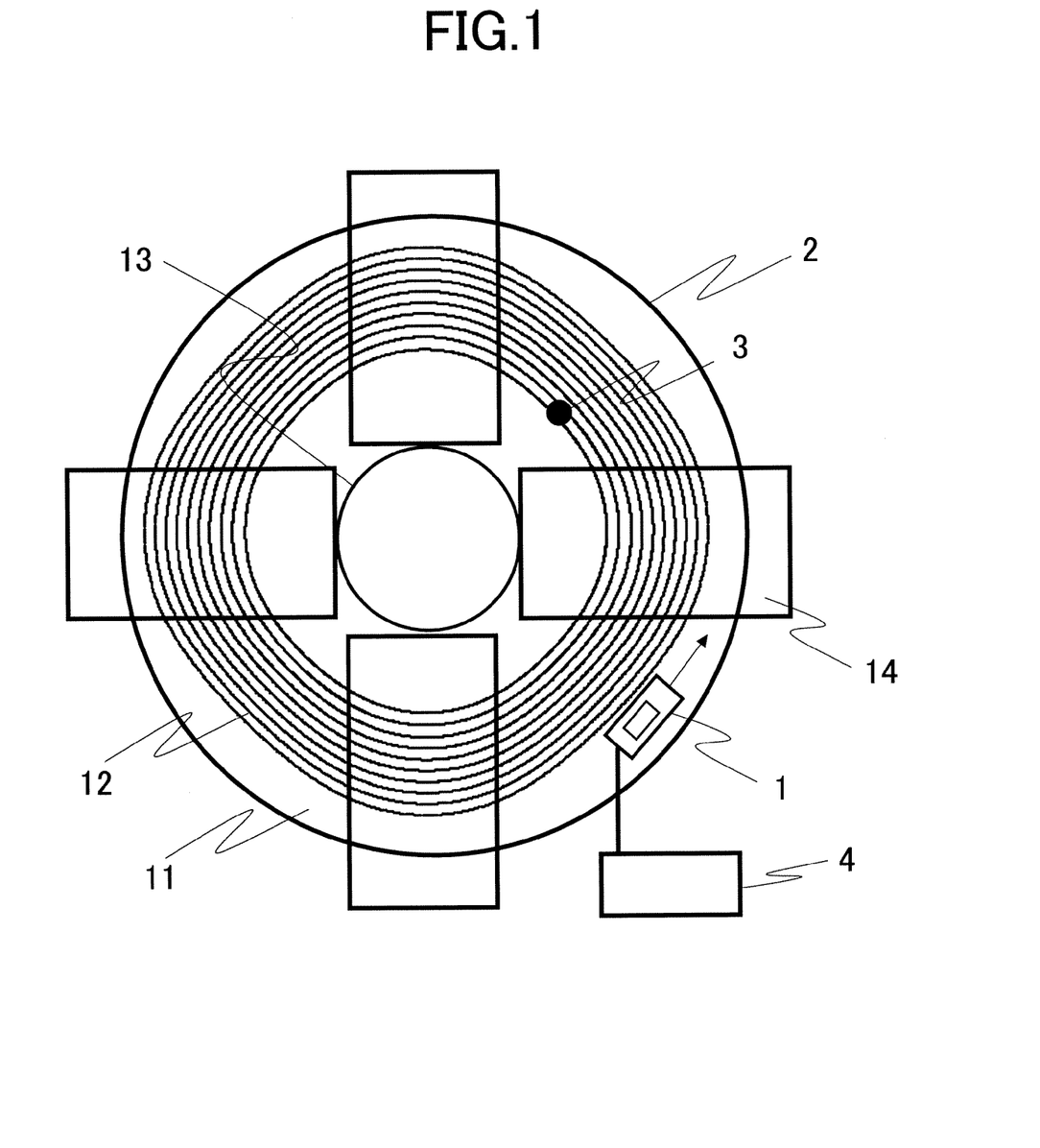
FIG. 1 is a sectional view of an electromagnetic wave generator according to Embodiment 1 of the present invention.

FIG. 1 illustrates an electromagnetic wave generator, according to Embodiment 1, equipped with a circular acceleration apparatus using a hybrid accelerator as the circular accelerator; FIG. 1 is also a sectional view taken on an orbital plane in which electrons move in orbits. In FIG. 1, "1" is an electron generator for generating electrons, "2" is a circular accelerator-a hybrid accelerator is exemplified in the figure—for injecting thereinto the electrons generated by the electron generator 1 and for accelerating the electrons up to a predetermined energy while making them move in orbits. "3" is an electromagnetic-wave-generation target that is placed in the way of an electron orbit in the circular accelerator 2, and the electrons accelerated up to the predetermined energy collide with the target 3 in order to generate electromagnetic waves such as X-rays. "4" is a high voltage power supply that applies the pulsed voltage to the electron generator 1 for generating electrons. All of the above-described components constitute the electromagnetic wave generator.

The components in the circular accelerator 2 (hereinafter, a hybrid accelerator is exemplified as the circular accelerator) will be described in detail below. "11" is a vacuum chamber in which the electrons orbit; "12" are orbits in which the electrons move in the vacuum chamber 11, and spread radially as shown in the figure. Here in the figure, each of the orbits 12 is illustrated as a closed orbit; however as will be described later in detail, because the orbiting electrons are being accelerated, they may move in the same fixed orbits or in orbits continuously changing in a spiral fashion in response to strength change with time of a deflection magnetic field. However, even if the change occurs, the amount of radius change per turn is in general imperceptible; approximately closed orbits 22 are configured. Therefore, hereinafter, the term "closed" will be used to imply the above meaning as well. In addition, the electron orbits illustrated in the figure are the ones in which electrons can move stably; other stable orbits can exist between the ones illustrated in the figure. "13" is an electron acceleration unit for accelerating electrons moving in the orbits 12 in the circular accelerator 2, "14" is an electron deflection unit for deflecting, in a plane formed by the orbits 12, the electrons that are moving and being accelerated. With a power supply, the electron acceleration unit 13 and the electron deflection unit 14 generate alternating magnetic fields having frequencies ranging from 50 hertz to several dozen kilohertz, they will be referred hereinafter to as an acceleration magnetic field and a deflection magnetic field, respectively.

As have been described, the electrons having been generated by the electron acceleration unit 1 are injected into the circular accelerator 2, undergo deflection force from the deflection magnetic field while passing through the electron deflection unit 14, and move in the closed orbits 12 in the vacuum chamber 11. While the electrons are moving in orbits, they are accelerated, when passing through the electron acceleration unit 13, by the electric field induced from the acceleration magnetic field generated by the electron acceleration unit 13; the radii of the orbits can be changed in response to the strength of the deflection magnetic field that is generated by the electron deflection unit 14 and changes with respect to time. Electrons having reached a predetermined energy level by being accelerated are controlled, using the above-described method, to move into an orbit where the target 3 is placed for generating electromagnetic waves such as X-rays, so that the electrons collide with the target 3 so as to generate electromagnetic waves such as X-rays in an electron-moving direction.

Figure 2A:
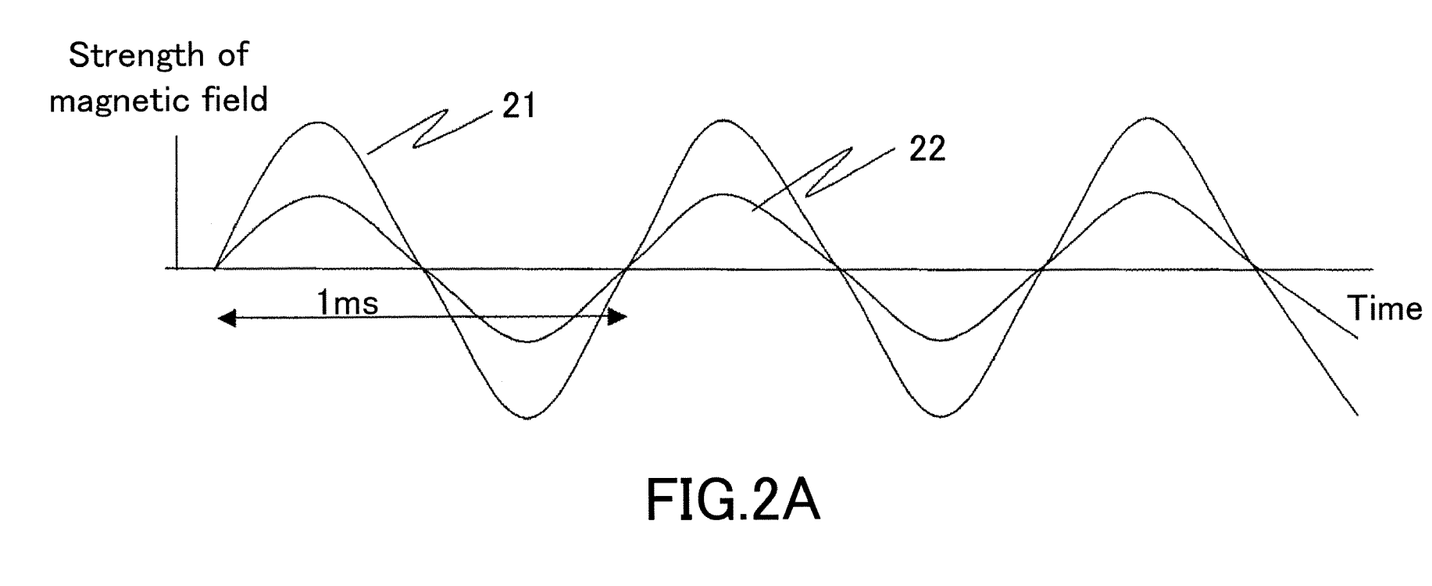
FIG. 2A is a diagram of waveforms of electromagnetic fields generated by an electron acceleration unit and an electron deflection unit in a circular accelerator according to Embodiment 1 of the present invention.
Figure 2B:
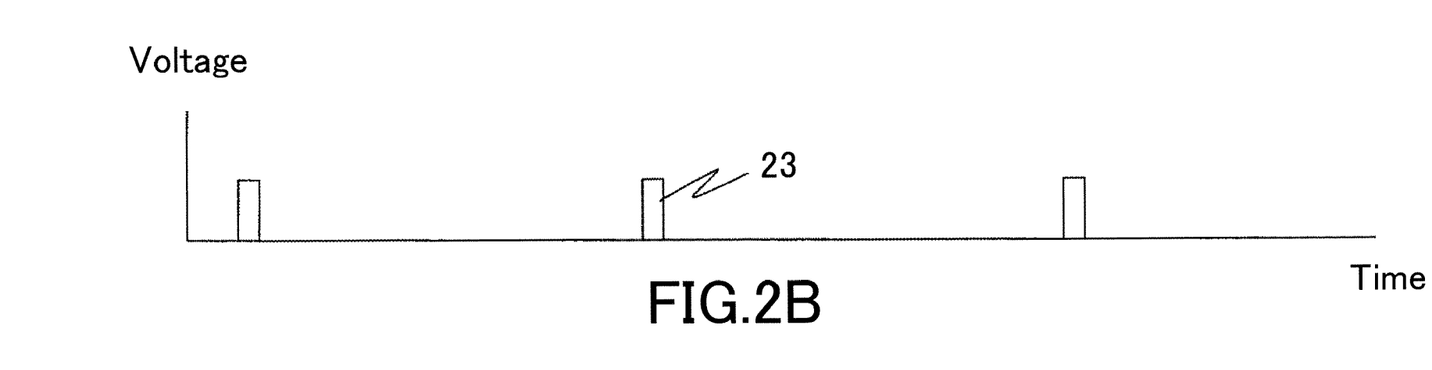
FIG. 2B is a diagram illustrating intervals of voltages applied to an electron generator in the circular accelerator according to Embodiment 1 of the present invention.
Figure 3:
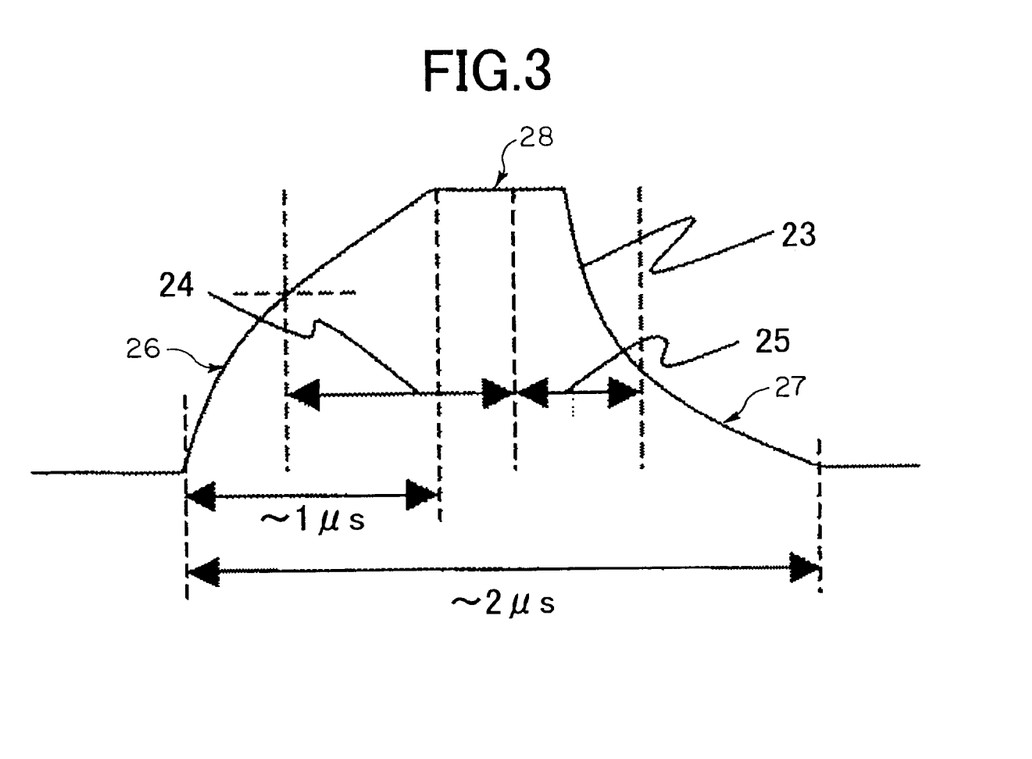
FIG. 3 is a diagram illustrating the waveform of a pulsed high-voltage that is applied to electron generator according to Embodiment 1 through Embodiment 3 of the present invention.

Next, the manner of the injection into the circular accelerator 2 of electrons generated by the electron generator 1 will be described, using FIG. 2. In FIG. 2, waveforms of acceleration-magnetic-field strength 21 generated by the electron acceleration unit 13 in the circular accelerator 2, deflection-magnetic-field strength 22 generated by the electron deflection unit 14, and a pulsed high voltage 23 applied to the electron generator 1 for generating electrons are illustrated with respect to time. FIG. 3 is an enlarged view of the pulsed high voltage 23. The energy of the electrons generated by the electron generator 1 depends on the value of the pulsed high voltage 23 applied thereto.

It is assumed that the waveforms of the acceleration-magnetic-field strength 21 and deflection-magnetic-field strength 22 are similar to each other, such as approximately sinusoidal wave patterns that change with time. In this case, adjusting to predetermined lengths the gaps between magnetic poles of the electron acceleration unit 13 and between those of the electron deflection unit 14, it becomes possible that both units share a power supply. Thereby, it also becomes unnecessary to control, in a complex manner, deflection-magnetic-field strength as illustrated in FIG. 10, so that a power supply can be manufactured at very low costs. When magnetic fields are controlled, as described above, by waveforms similar to each other, the deflection-magnetic-field strength increases in a manner similar to the acceleration-magnetic-field strength during injection periods; radial change of the electron orbits during injection periods becomes less than the case shown in FIG. 10. Therefore, radii of the electron orbits during injection periods are expanded less than the case shown in FIG. 10; the density of electrons becomes relatively high. To avoid the situations above, fluctuations of electron energies at injection are deliberately increased greatly in the electromagnetic wave generator according to this embodiment; thereby, the radii of electron orbits are expanded even in those situations, intending that the density of electrons is lowered. Using FIG. 2 and FIG. 3, details thereabout will be described below.

In FIG. 2, after the strength of the magnetic field 21 generated by the electron acceleration unit 13 and that of the magnetic field 22 generated by the electron deflection unit 14 have risen to predetermined values, the pulsed high voltage 23 illustrated in FIG. 3 is applied to the electron generator 1. The pulsed high voltage is not the one that has been generally applied to the electron generator 1, but has a slowly-rising edge 26. Each of the electrons generated by the electron generator 1 in FIG. 1 has its own energy corresponding to an instantaneous value of the pulsed high voltage 23. The waveform of the pulsed high voltage has the dulled rising edge, which is generated in the high voltage power supply. Shown in FIG. 3, the waveform of the pulsed high voltage 23 applied to the electron generator 1 is formed to rise slowly up to its peak 28, for example, within some one microsecond. Meanwhile, in the circular accelerator, there exists a range of injection energy that allows the electrons to be accelerated stably after having been injected. As have been described above, electrons generated by the electron generator 1 obtain energies depending on a pulsed high voltage value; the peak value of the pulse is determined such that it copes with the upper limit value in the rage of injection energy. Meanwhile, the lower limit value in the rage of injection energy corresponds to a predetermined voltage value, as shown in FIG. 3, on the waveform of the pulsed voltage rising slowly. Furthermore, there exists an upper limit of an injection period in the circular accelerator 2; this is because that injecting for too long period causes injected electrons to move unstably in orbits. Taking into account of the conditions above, while the pulsed high voltage 23 in FIG. 3 is being applied, an injection period is to be determined so that the electrons move stably in orbits after having been injected. This injection period is indicated as a first injection period 24 in FIG. 3. Therefore, while the pulsed high voltage 23 is being applied, electron energy generated in response to the waveform during the first period 24 is low in the initial part of the period, but increases high with passage of time; each of the electrons is injected into the circular accelerator 2 every time it is generated. Electrons of low energies are injected in the initial part of the period and accelerated therefrom so as to have larger energies; therefore, their energies become close to those of electrons injected during the later part of the period within the first injection period 24. However, even under such circumstances, it is possible to ensure that the electron orbits are sufficiently spread out. When the acceleration-magnetic-field strength 21 and the deflection-magnetic-field strength 22 are correlated with each other in such a manner that, when the electrons have a constant energy at each injected instant, if the electrons are made to move in a fixed orbit without regard to each injected instant, the electron orbits spread out radially due to energy differences among the injected electrons. In both cases, without taking complex control of the acceleration-magnetic-field strength 21 and deflection-magnetic-field strength 22, it is possible that the radii of the electron orbits are easily expanded by slowly raising the leading edge of the pulsed high voltage 23 applied to the electron generator 1; therefore, spatial charge of the electrons can be reduced, so that one of the initial aims to increase current can be achieved. Meanwhile, in the conventional application of pulsed voltage to the electron generator 1, injection of electrons begins when the pulsed voltage reaches a constant voltage, and ends at an instant during the period in which the pulsed voltage is yet maintained at the constant voltage; that is, it is basically assumed that electrons having a constant energy are injected. The electromagnetic wave generator according to the embodiment differs completely from the related arts in that injection begins at an instant before the pulsed voltage reaches a constant voltage or continues until an instant after the voltage has reached the constant voltage.

Therefore, while the pulsed high voltage 23 is being applied, electron energy generated in response to the waveform during the first period 24 is low in the initial part of the period, but increases high with passage of time; each of the electrons is injected into the circular accelerator 2 every time it is generated. Electrons of low energies are injected in the initial part of the period and accelerated therefrom so as to have larger energies; therefore, their energies become close to those of electrons injected during the later part of the period within the first injection period 24. However, even under such circumstances, it is possible to ensure that the electron orbits are sufficiently spread out. When the acceleration-magnetic-field strength 21 and the deflection-magnetic-field strength 22 are correlated with each other in such a manner that, when the electrons have a constant energy at each injected instant, if the electrons are made to move in a fixed orbit without regard to each injected instant, the electron orbits spread out radially due to energy differences among the injected electrons. In both cases, without taking complex control of the acceleration-magnetic-field strength 21 and deflection-magnetic-field strength 22, it is possible that the radii of the electron orbits are easily expanded by slowly raising the leading edge of the pulsed high voltage 23 applied to the electron generator 1; therefore, spatial charge of the electrons can be reduced, so that one of the initial aims to increase current can be achieved. Meanwhile, in the conventional application of pulsed voltage to the electron generator 1, injection of electrons begins when the pulsed voltage reaches a constant voltage, and ends at an instant during the period in which the pulsed voltage is yet maintained at the constant voltage; that is, it is basically assumed that electrons having a constant energy are injected. The electromagnetic wave generator according to the embodiment differs completely from the related arts in that injection begins at an instant before the pulsed voltage reaches a constant voltage of continues until an instant after the voltage has reached the constant voltage.

Figure 6:
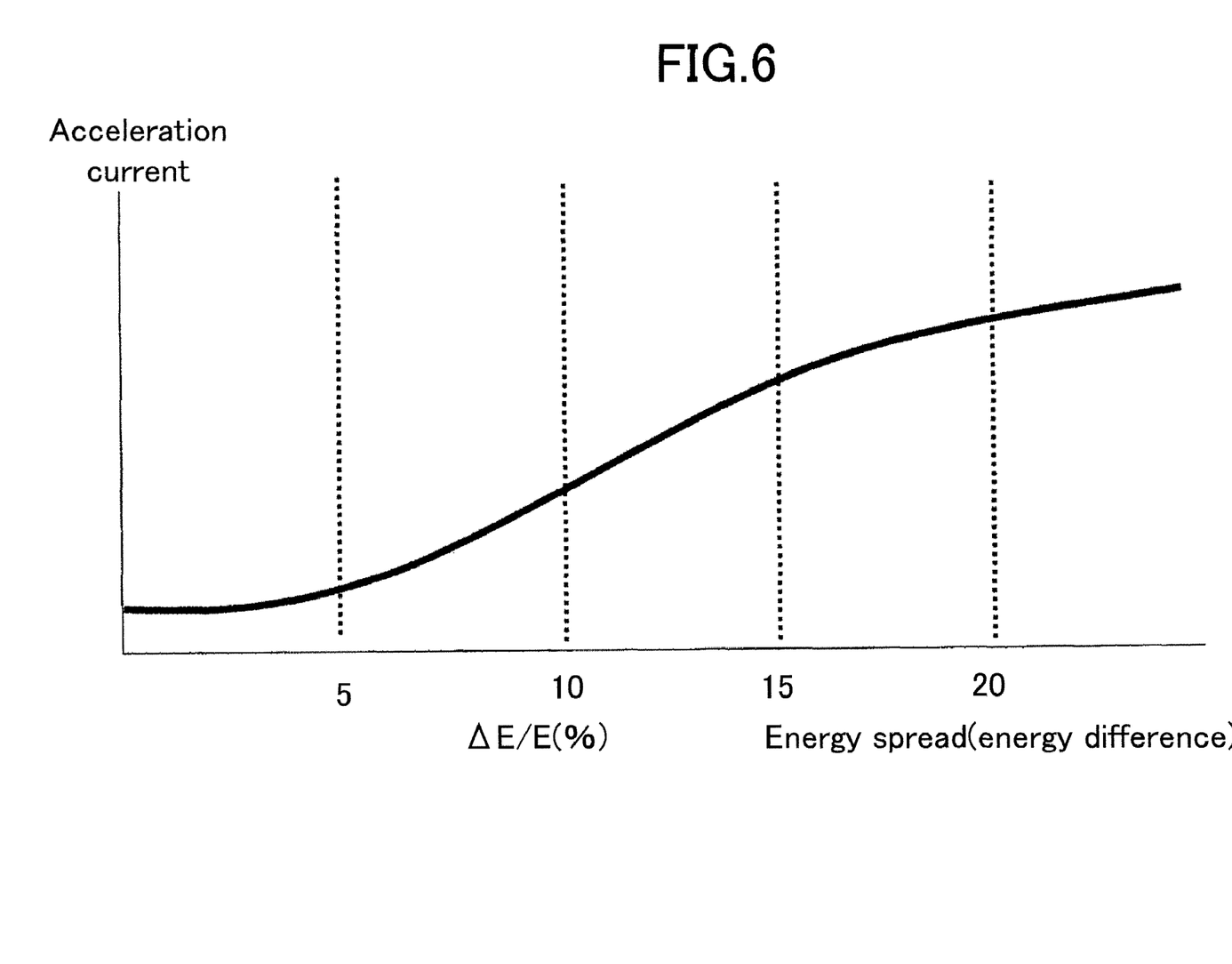
FIG. 6 is a diagram illustrating a relation of how energies of the electrons generated by the electron generator spread with respect to acceleration current in the circular accelerator according to Embodiment 1 of the present invention.

Using FIG. 6 as an example, an extent to which a current is increased will be explained as follows. FIG. 6 shows results of simulation calculation of an acceleration current, taking as a parameter energy spread (energy difference) of electrons injected into the circular accelerator 2, when the acceleration-magnetic-field strength 21 and the deflection-magnetic-field strength 22 are controlled so that orbits are not changed by acceleration. As seen from in the figure, as energies of electrons injected spread, the maximum value of the acceleration current increases. However, remarkable increase is not found in an energy spread range of below five percent, the reason for which is that stable orbits corresponding to each of the energies differ a little from each other in the energy spread range of below five percent; a beam size itself corresponding to each energy is considered as a dominant factor that determines spatial charge effect. In an energy spread range of over five percent, acceleration-possible current increases dramatically; it almost linearly increases until the energy spread reaches 15 percent thereof, as the energy spread increases; beyond that energy spread, the acceleration current increases gradually again. This is because, with energy spread being widened too much, some of the electrons move beyond a stable orbit region of the circular accelerator 2, so that they do not move stably in orbits. In FIG. 6, it is found that acceleration current can be increased up to five times as much or more. Furthermore, depending on a design of the accelerator, it is also possible to increase the acceleration current up to ten times as much or more.

Next, in order to generate electromagnetic waves such as X-rays, it is necessary for electrons moving in orbits to collide with the electromagnetic-wave-generation target 3. In the example shown in FIG. 1, the electron generator 1 is disposed in the outer side of the circular accelerator 2, so that electrons are injected from the circumference thereof, meanwhile, the electromagnetic-wave-generation target 3 is disposed in the inner side of the circular accelerator 2. Under the circumstances in which the acceleration-magnetic-field strength 21 and the deflection-magnetic-field strength 22 change with respect to time, as shown in FIG. 2, presetting the strength ratio of them at a predetermined value, the radii of the electron orbits can be reduced radially inward during their acceleration, depending on the value. As has been described above, the radii of the electron orbits that have been expanded radially in the circular accelerator 2 can be gradually reduced inward by fixing the relation between the acceleration-magnetic-field strength 21 and the deflection-magnetic-field strength 22 at a predetermined one; the electrons can collide with the electromagnetic-wave-generation target 3 so that electromagnetic waves such as X-rays are continuously generated during a period in which the radii of the orbits are reduced depending on each distance (to the target). A similar effect can be obtained, when the radii of the orbits are changed by adding perturbation to the deflection magnetic field at the time of acceleration completion, so that electrons collide with the electromagnetic-wave-generation target 3. As has been described, it is possible for the electron beams having increased current to collide with the electromagnetic-wave-generation target 3; even when the electromagnetic-wave-generation target 3 becomes smaller, electromagnetic waves such as X-rays of strength commensurate to the current can be generated. That is, it becomes possible to realize high brilliance electromagnetic waves.

So far, a hybrid accelerator has been exemplified as the circular accelerator 2; however, a circular accelerator is not limited to the hybrid accelerator. As long as an accelerator can stably accelerate injection electrons having energies in a certain range, the accelerator can bring effects similar to that described above; synchrotron accelerators and betatron accelerators are examples of those.

However, the degree of improvement in increasing current differs depending on types of accelerators, because each type has its own range of allowable injection energy. In addition, the above explanations have been made on the assumption that the electron acceleration unit 13 uses inducted magnetic field acceleration in which electrons are accelerated by an electric field generated from an acceleration magnetic field. However, the above-described method is not limited to only the induced magnetic field acceleration, but also may be applied intact to high frequency electric field acceleration. In that case, replacing the acceleration-magnetic-field strength 21 in FIG. 2 with an acceleration-electric-field strength, the above description holds true.

Embodiment 2

Figure 4:
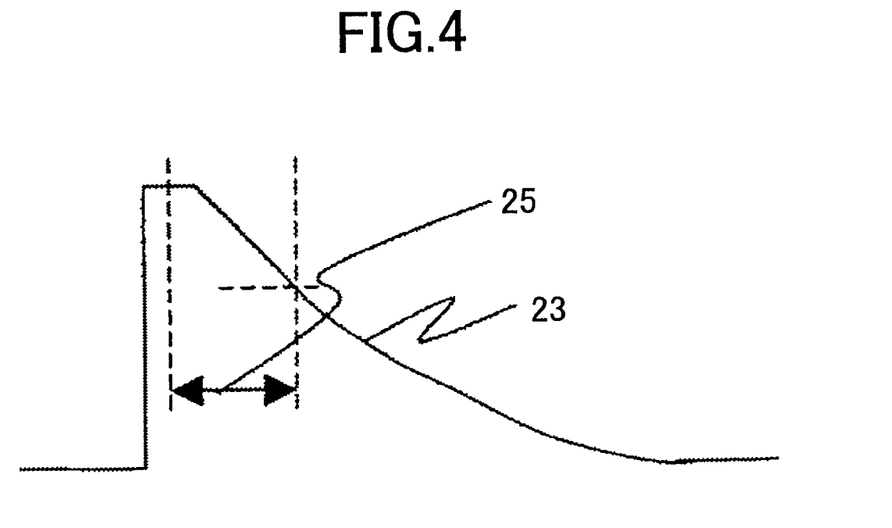
FIG. 4 is a diagram illustrating the waveform of a pulsed high-voltage that is applied to the electron generator according to Embodiment 2 of the present invention.

In the present embodiment, the pulsed high voltage 23 applied to the electron accelerator 1 has a slow falling edge 27, and electrons generated during this slow falling period are injected into the circular accelerator 2. The waveform of the pulsed high voltage has the dulled falling edge, which is generated in the high voltage power supply. When a second injection period 25 shown in FIG. 3 is used as an injection period, it is also possible to use electrons with lower energies that have been generated during the period of the falling edge of the pulsed high voltage 23. FIG. 4 is a diagram illustrating an example of a waveform of a pulsed high voltage 23 according to the embodiment. Because the falling edge of the pulse is used, any rising edge of the pulse is not critical. In the figure, a pulsed high voltage that rises steeply as in a conventional manner is shown. In the figure, '25' indicates a second injection period that is determined under constraints of an injection energy range and an injection period needed for stable acceleration. That is, the second injection period starts at an instant during a period in which the voltage holds its peak, and continues until a predetermined instant during a period of the voltage falling. In each of FIG. 3 and FIG. 4, a high voltage applied to the electron generator 1 is initially high, and then becomes lower with a lapse of time; in response to the voltage, electrons having high energies are initially injected into the circular accelerator 2, and then those having low energy are injected thereinto with a lapse of time. Therefore, when injection is completed, the energies of injection electrons spread differently from that in FIG. 3; the energy differences become larger than those at their injection; accordingly, orbits of injected electrons spread out radially. As has been described above, the waveform of the pulsed high voltage 23 can be made to slowly fall at the falling edge and a period corresponding to the edge is used to inject electrons, so that the radii of electron orbits can also be expanded; therefore, it is possible to increase current in the circular accelerator similarly to Embodiment 1. Therefore, using a circular acceleration apparatus as described above, it becomes possible to intensify electromagnetic waves such as X-rays generated by electromagnetic-wave generators such as X-ray ones.

Embodiment 3

In this embodiment, the injection period includes both of the first injection period 24 and the second injection period 25 in FIG. 3. Because the embodiment brings both effects described in Embodiment 1 and Embodiment 2, the radii of the electron orbits can also be expanded, so that it is possible to increase current in the circular accelerators similarly to Embodiment 1. Therefore, using a circular acceleration apparatus as described above, it becomes possible to intensify electromagnetic waves such as X-rays generated by electromagnetic-wave generators such as X-ray ones. However, as has been described, the injection period has an upper limit; in some cases, the periods each described in Embodiment 1 and Embodiment 2 can not be simply combined. In those cases, the overall pulse width may be narrowed so that the combination of both periods is permissible as the injection period.

Embodiment 4

In this present embodiment, a means will be described below in which the pulsed high voltage 23 shown in FIG. 3 is applied to the electron generator 1. Conventional high voltage sources used for betatron accelerators and such generate pulsed voltage by charging a capacitor with electricity generated by a high voltage generator and switching the charge with a vacuum tube such as a thyratron. However, the problem has been that the high voltage sources become bulky and expensive, and the vacuum tube needs to be replaced frequently. In this embodiment according to the present invention, the pulsed high voltage shown in FIG. 3 can be generated by a simple power-supply circuit shown in FIG. 5.

Figure 5:
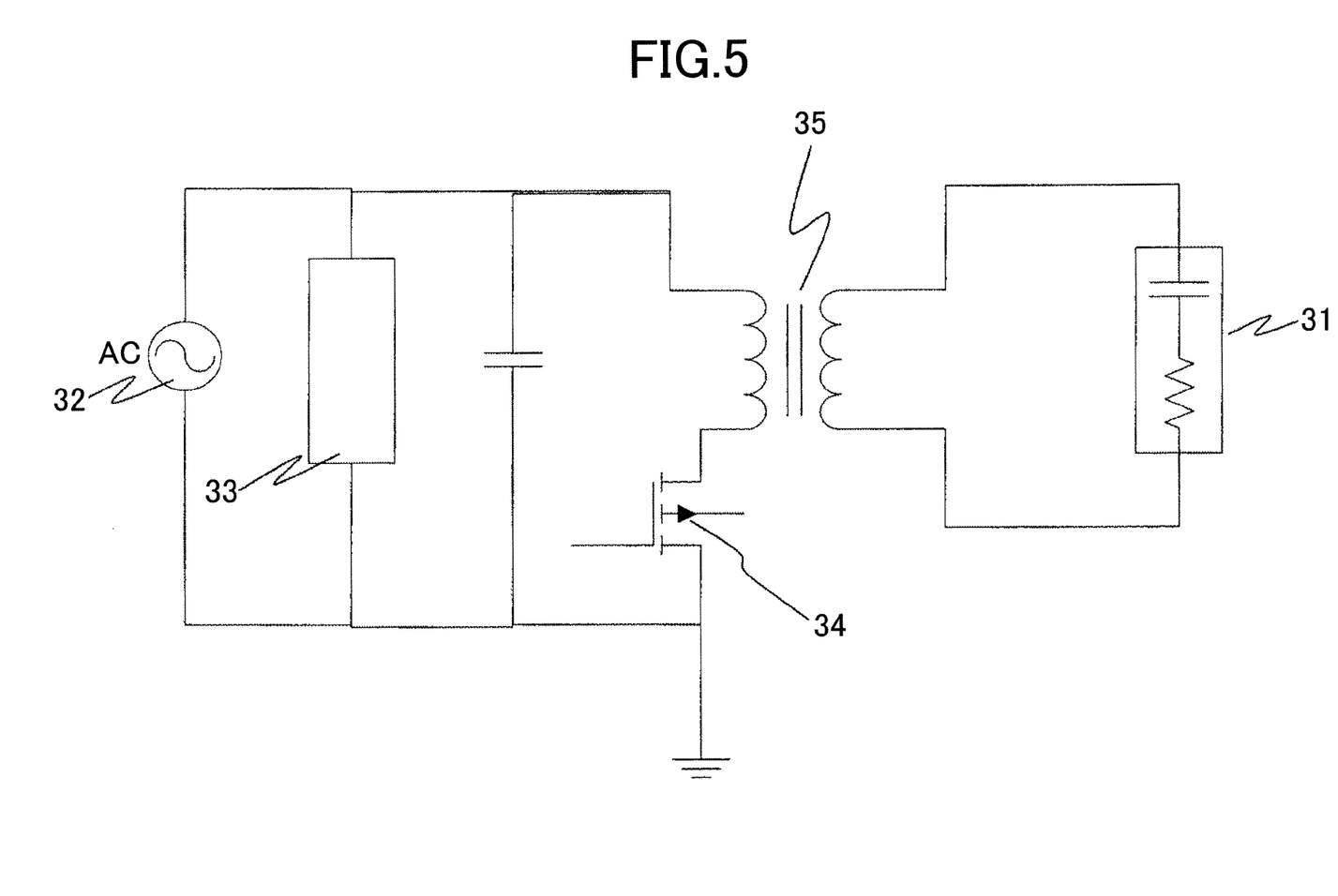
FIG. 5 is an outlined circuit diagram of a high voltage power source that applies a high voltage to an electron generator according to Embodiment 4 of the present invention.

In order for an equivalent circuit 31 of the electron generator 1 to generate predetermined high voltage pulses, low voltage pulses are first generated. That is, an AC-voltage from an AC-power supply 32 is converted into a DC-voltage with rectifying/smoothing circuits 33, and the predetermined low voltage pulses are generated from the DC-voltage by a switching device 34 such as an insulated gate bipolar transistor (IGBT) or a metal oxide semiconductor field effect transistor (MOS-FET); then the pulses are stepped up into high voltage pulses through a high voltage transformer 35. Because pulses are formed in the low voltage side thereof, it is easy to form the pulses into the ones of any waveform, and the voltage transformer 35 can make the voltage rise slowly and can make the voltage increase monotonically at its rising edge; therefore, the pulsed high voltage 23 shown in FIG. 3 can easily be formed. In addition, the circuit that generates the pulses can be configured with only low-price elements; therefore, manufacturing costs of the pulsed high voltage source can be dramatically reduced.

Embodiment 5

Figure 7:
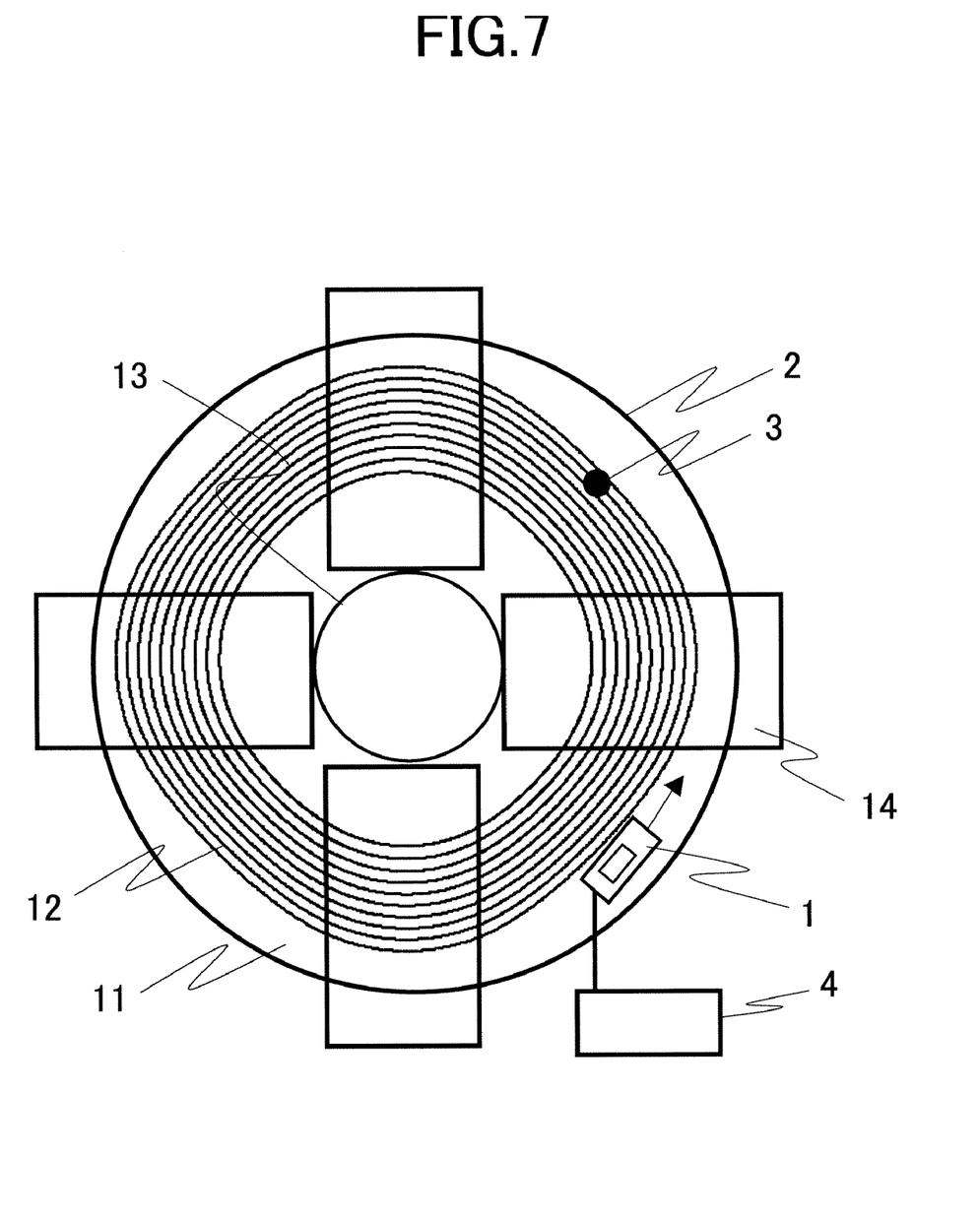
FIG. 7 is a sectional view of an electromagnetic wave generator according to Embodiment 5 of the present invention.

In Embodiment 1, the electromagnetic-wave-generation target 3 is displaced in an inner-side orbit of the electron orbits 12; the same effects as those in Embodiment 1 can be obtained when the target is disposed, as shown in FIG. 7, in an outer-side orbit thereof. With an electromagnet power supply, the electron acceleration unit 13 and the electron deflection unit 14 generate AC magnetic fields having frequencies between 50 hertz and several dozen kilohertz; when the relation between magnetic field strengths of both the magnetic fields is set to a predetermined value, the electron beams do not change their orbits largely, so that the electron beams are stably accelerated within a region. The electron beams having been accelerated are shifted outward in response to slight change of the relation between magnetic field strengths of the electron acceleration unit 13 and the electron deflection unit 14; the electron beams collide with the electromagnetic-wave-generation target 3 disposed in the way of an orbit in a stably orbiting region, so that electromagnetic waves such as X-rays are generated. Here, when the target 3 is disposed in the outer portion of the accelerator, part of the electron beams collide with the target 3 immediately after their injection. However, as long as the target 3 is on the order of several micrometers, the number of electrons that collide with the target 3 when injected is small, and most of them can be stably accelerated.

In that case, the electron beams are accelerated in a region inward from the location of the target 3 for generating electromagnetic waves such as X-rays. After the acceleration has been finished, the radii of the electron beam orbits are enlarged so that electrons are shifted to reach the target 3 for generating electromagnetic waves such as X-rays. Detailed explanations of shifting the beams and generating electromagnetic waves such as X-rays are the same as those in Embodiment 1. In addition, when electromagnetic waves such as X-rays are generated in a region close to the outer circumference of the circular accelerator, the generating source that generates electromagnetic waves such as X-rays is disposed closer to an irradiation target than the case in which electromagnetic waves such as X-rays are generated in a region near to the center of the accelerator; therefore, it becomes possible to increase irradiation density and shorten the period of irradiation. Furthermore, it becomes easy to increase imaging magnification. Increase of imaging magnification can be realized by distancing the irradiation target apart from an imaging screen. Given that R1 is a distance between the irradiation target and the generating source that generates electromagnetic waves such as X-rays, R2, a distance between the irradiation target and the imaging screen, the imaging magnification is R2 divided by R1. Because R1 can be made smaller while keeping R1+R2 constant, the imaging magnification becomes large. On the contrary, when R1 is large in the first place, R2 must be increased in order to achieve a high imaging magnification, which causes a problem in that not only a large area is needed to install the imaging system, but also, because the imaging area becomes large, the strength of electromagnetic waves per area that can be used for imaging becomes low, so that statistical accuracy in imaging data is decreased. In a case where R1 is kept small, an irradiation area becomes small by that much.

Embodiment 6

Figure 8:
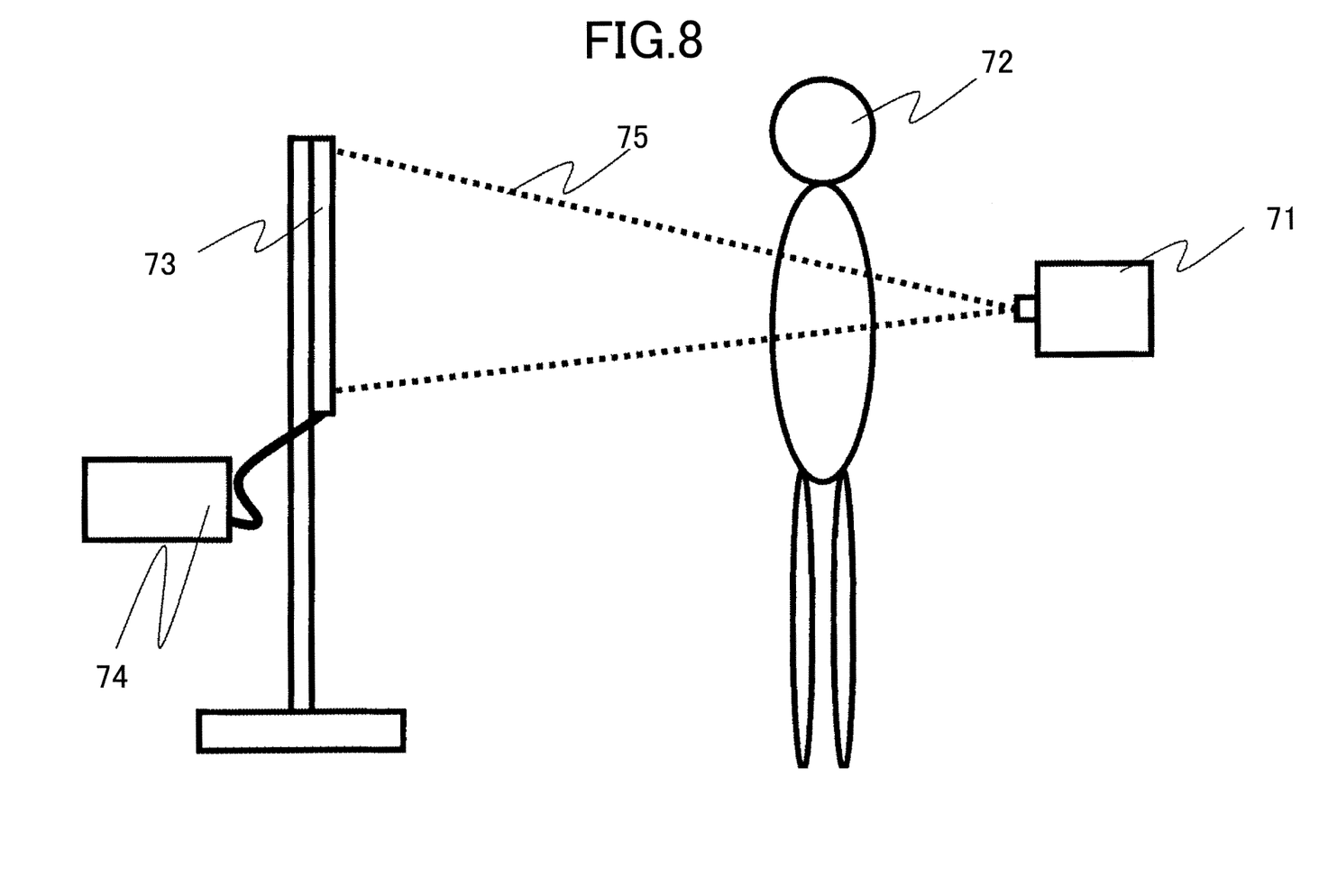
FIG. 8 is an outlined configurational diagram of an X-ray imaging system according to Embodiment 6 of the present invention.

FIG. 8 is an outlined configurational diagram of an X-ray imaging system (an electromagnetic-wave imaging system, in broad sense) according to this embodiment. The imaging system includes an electromagnetic wave generator 71, a subject-a human body 72 here, an image detector 73, and a data processing unit 74. Intensified X-rays 75 that have been generated by the electromagnetic wave generator 71 are incident on the human body 72, are detected by the image detector 73, and then are processed by the data processing unit 74 so as to produce a radioscopic image. Because the electromagnetic wave generator 71 can generate intensified X-rays whose radiation-source size ranges from several micrometers to approximately dozen micrometers, refraction-contrast imaging can be implemented in which minute refractions in X-rays are used. Because of small refraction effects, this method has not been implemented until the size of radiation source becomes sufficiently small. However, provided that the size of radiation source is small, the X-ray strength is generally decreased; it has been difficult to produce images with sufficient statistical accuracy. Therefore, conventionally, the method has only been realized in a high intensified-synchrotron-radiation generator—such as Super Photon ring 8 GeV (SPring8)—having a diameter of several hundreds meters, so that progress has not been made in medical use; however, refraction-contrast images can be obtained by using an electromagnetic wave generator 71, according to the present invention, whose size is almost equal to or smaller than that of a conventional X-ray tube; therefore, medical use of the method is expected to be promoted. Using the method of refraction-contrast imaging, mixture of minute materials having different mass-densities can be imaged with their boundaries being reinforced, and enlarged images of them can also be obtained; therefore, it is possible to perceive a small cancer of approximately several millimeters. In addition, because the images taken by the refraction-contrast imaging method can realize contrast ten times as high as those by the conventional absorption-contrast imaging method, the images can be taken with a subject being exposed to a radiation dose of approximately one tenth of that compared to conventional imaging methods.

Figure 9:
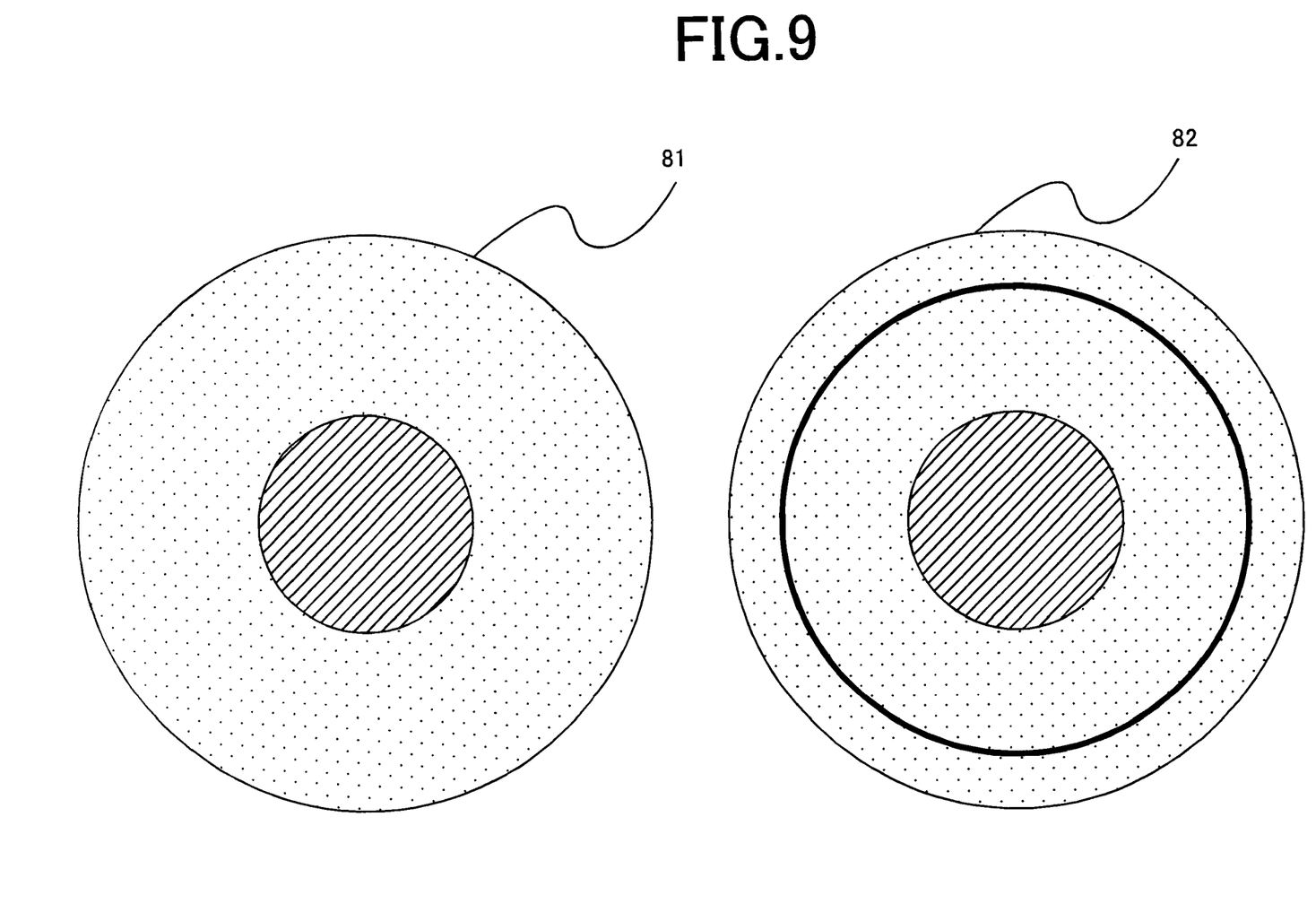
FIG. 9 illustrated simulation results of images of a sphere having a diameter of one millimeter, taken by the X-ray imaging system according to Embodiment 6 of the present invention.

FIG. 9 shows a result, in which the system shown in FIG. 8 has simulated a radioscopic image of a sphere of one millimeter diameter, made of water-equivalent material, which is assumed as a small cancer. It is assumed that the size of target is ten micrometers; an acceleration energy of the electron beams is one mega-electron volt; a beam current value is, when $\Delta E/E$ of the injection beam is 15 percent, two amperes. '81' is a conventional absorption-contrast image, '82', a refraction-contrast image. A circular line that appears well-defined in the refraction-contrast image 82 is a boundary of the water-equivalent sphere, and difference from the one in the absorption-contrast image 81 is pronounced. The refraction-contrast imaging method above-described can be used only because its radiation source is small and has high strength. Herewith, a meaning has been verified in which a radiation source according to the present invention is used as the one for X-ray imaging systems. This holds true not only for X-rays, obviously, but also for all other electromagnetic waves.

Furthermore, human bodies are not only the imaging subjects of the X-ray imaging systems; for example, when producing a radioscopic image of a power semiconductor device by the systems provided with the refraction-contrast imaging method, aluminum wirings in the device can be perceived by the refraction-contrast imaging method, in which the wirings have not been perceived by the conventional absorption-contrast imaging method. Because the refraction-contrast imaging method can distinguish two kinds of materials whose atomic numbers are close to each other, the method can also distinguish aluminum wirings whose atomic number is close to that of silicon.

Although, in the above explanation, the circuit element, which dulls at least one edge of the rising and the falling edge of the pulsed high voltage, has been provided in the high voltage power supply, the circuit element may be provided outside of the high voltage power supply.

According to these embodiments, because a simplified high voltage power supply is adopted, it is possible to obtain a circular acceleration apparatus that can accelerate higher currents as well as avoid complex controlling of a deflecting magnetic field generated by an electron deflection unit. Also, applying the circular acceleration apparatus to an electromagnetic wave generator and an electromagnetic-wave imaging system using the electromagnetic wave generator, a generator that can generate intensified electromagnetic waves such as X-rays and an electromagnetic-wave imaging system that has a high resolution can be obtained.

Although, as described above, the embodiments according to the present invention have been explained with referring to the figures, specific structures are not limited to these embodiments, but other structures may be included in the invention without departing from the spirit and scope thereof.

What is claimed is:

1. A circular acceleration apparatus comprising:
    a circular accelerator including an electron acceleration unit accelerating injected electrons, and a deflection-magnetic-field generating unit deflecting the orbits of the electrons accelerated by said electron acceleration unit;
    an electron generator, to which a pulsed voltage is applied, to generate electrons for injecting to said circular accelerator in respond to the pulsed voltage; and
    a circuit element which generates the pulsed voltage for providing to said electron generator by making the pulsed voltage applied to the electron generator have at least one of a slow rising edge to its peak and a slow falling edge from its peak.

2. A circular acceleration apparatus according to claim 1, wherein said circuit element generates the pulsed voltage for providing to said electron generator by dulling at least one of rising and falling edge of the waveform of the pulsed voltage generated by a high voltage power supply.

3. A circular acceleration apparatus according to claim 1, comprising a high voltage power supply, and wherein said high voltage power supply includes said circuit element.

4. A circular acceleration apparatus according to claim 1, wherein electrons generated based on the voltage of the rising or falling edge of the said pulsed voltage, are injected into said circular accelerator.

5. A circular acceleration apparatus according to claim 1, wherein electrons generated for the rising period where the value of voltage increases, are injected into said circular accelerator.

6. A circular acceleration apparatus according to claim 1, wherein electrons generated for the falling period where the value of voltage decreases, are injected into said circular accelerator.

7. A circular acceleration apparatus according to claim 5, wherein electrons generated for the peak-value period where the peak value of the voltage maintains, are also injected into said circular accelerator.

8. A circular acceleration apparatus according to claim 6, wherein electrons generated for the peak-value period where the peak value of the voltage maintains, are also injected into said circular accelerator.

9. A circular acceleration apparatus according to claim 1, wherein said electron acceleration unit accelerates electrons through induction acceleration.

10. A circular acceleration apparatus according to claim 3, wherein said high voltage power supply has a low voltage pulse generating circuit generating a low voltage pulse, and said circuit element has a transformer connected to said low voltage generating circuit, to generate said pulsed voltage for providing to said electron generator by the pressure rising of the low voltage pulse.

11. A circular acceleration apparatus according to claim 10, wherein said low voltage pulse generating circuit includes an AC voltage source, rectifying/smoothing circuit connected to AC voltage source to convert the AC voltage supplied from said AC voltage source to the DC voltage, and a switching device connected to said rectifying/smoothing circuit to generate said low voltage pulse by switching.

12. A circular acceleration apparatus according to claim 1, wherein the waveform of the strength of magnetic field generated by said electron acceleration unit is similar to that of magnetic field generated by said deflection-magnetic-field generating unit.

13. A circular acceleration apparatus according to claim 12, wherein said waveform of the strength of magnetic field generated by said electron acceleration unit has the same phase and period as that of magnetic field generated by said deflection-magnetic-field generating unit.

14. A circular acceleration apparatus comprising:
    a circular accelerator including an electron acceleration unit accelerating injected electrons, and a deflection-magnetic-field generating unit deflecting the orbits of the electrons accelerated by said electron acceleration unit; and
    an electron generator, to which a pulsed voltage is applied, to generate electrons for injecting into said circular accelerator based on the voltage of a slow rising edge to its peak or a slow falling edge of said pulsed voltage from its peak.

15. An electromagnetic wave generation apparatus comprising:
    a circular acceleration apparatus including
        a circular accelerator including an electron acceleration unit accelerating injected electrons and a deflection-magnetic-field generating unit deflecting the orbits of the electrons accelerated by said electron acceleration unit,
        an electron generator to which a pulsed voltage is applied to generate electrons for injecting to said circular accelerator in respond to the pulsed voltage, and
        a circuit element which generates the pulsed voltage for providing to said electron generator by making the pulsed voltage applied to the electron generator have at least one of a slow rising edge to its peak and a slow falling edge from its peak; and
    an electromagnetic-wave-generation target, placed in the way of an orbit in which electrons move stably in said circular accelerator for generating electromagnetic waves by collision with the electrons.

16. An electromagnetic wave imaging system comprising:
    a circular acceleration apparatus including
        a circular accelerator including an electron acceleration unit accelerating injected electrons and a deflection-magnetic-field generating unit deflecting the orbits of the electrons accelerated by said electron acceleration unit,
        an electron generator to which a pulsed voltage is applied to generate electrons for injecting to said circular accelerator in respond to the pulsed voltage, and
        a circuit element which generates the pulsed voltage for providing to said electron generator by making the pulsed voltage applied to the electron generator have at least one of a slow rising edge to its peak and a slow falling edge from its peak;
    an electromagnetic-wave-generation target, placed in the way of an orbit in which electrons move stably in said circular accelerator for generating electromagnetic waves by collision with the electrons;
    a measuring unit measuring said electromagnetic waves generated by the collision; and a data processing unit processing data measured by the measuring unit.

17. A circular acceleration apparatus comprising:

a circular accelerator including an electron acceleration unit accelerating injected electrons and a deflection-magnetic-field generating unit deflecting the orbits of the electrons accelerated by said electron acceleration unit; and an electron generator, to which a pulsed voltage is applied by a high voltage power supply, to generate electrons for injecting to said circular accelerator in response to the rising period of the said pulsed voltage where the value of voltage increases, or the falling period of the said pulsed voltage where the value of voltage decreases.

* * * * *